United States Patent
Bozic

(10) Patent No.: US 9,969,016 B2
(45) Date of Patent: May 15, 2018

(54) ROTARY RECIPROCATING SAW BLADE FOR A POWER TOOL

(71) Applicant: Robert Bosch GmbH, Stuttgart (DE)

(72) Inventor: Milan Bozic, Solothurn (CH)

(73) Assignee: Robert Bosch GmbH, Stuttgart (DE)

( * ) Notice: Subject to any disclaimer, the term of this patent is extended or adjusted under 35 U.S.C. 154(b) by 658 days.

(21) Appl. No.: 14/367,322

(22) PCT Filed: Nov. 7, 2012

(86) PCT No.: PCT/EP2012/071980
§ 371 (c)(1),
(2) Date: Jun. 20, 2014

(87) PCT Pub. No.: WO2013/091979
PCT Pub. Date: Jun. 27, 2013

(65) Prior Publication Data
US 2015/0000143 A1   Jan. 1, 2015

(30) Foreign Application Priority Data

Dec. 20, 2011   (DE) .......................... 10 2011 089 097

(51) Int. Cl.
| | | |
|---|---|---|
| *A61B 17/3213* | (2006.01) | |
| *B23D 61/00* | (2006.01) | |
| *A61B 17/14* | (2006.01) | |
| *B23D 65/00* | (2006.01) | |
| *B23D 61/02* | (2006.01) | |

(52) U.S. Cl.
CPC ............ *B23D 61/006* (2013.01); *A61B 17/14* (2013.01); *A61B 17/142* (2016.11); *A61B 17/3213* (2013.01); *B23D 61/025* (2013.01); *B23D 65/00* (2013.01)

(58) Field of Classification Search
CPC .. B23D 61/006; B23D 61/025; B23D 61/026; B23D 65/00; A61B 17/3213; A61B 17/14; A61B 17/142; A61B 17/144
USPC .................... 30/346, 348, 351; 606/176–178
See application file for complete search history.

(56) References Cited

U.S. PATENT DOCUMENTS 2,824,369 A * 2/1958 Welch .................... A47G 21/04
                                                              206/499
4,036,236 A * 7/1977 Rhodes, Jr. .......... B23D 61/123
                                                               30/348
(Continued)

FOREIGN PATENT DOCUMENTS

| CH | 695 483 A5 | 6/2006 |
|---|---|---|
| DE | 102 31 393 A1 | 1/2004 |

(Continued)

OTHER PUBLICATIONS

International Search Report corresponding to PCT Application No. PCT/EP2012/071980, dated Feb. 22, 2013 (German and English language document) (6 pages).

*Primary Examiner* — Phong Nguyen
(74) *Attorney, Agent, or Firm* — Maginot, Moore & Beck LLP

(57) ABSTRACT

A rotary reciprocating saw blade for a power tool comprises a blade body having an at least approximately rectilinear cutting edge, and at least two linear or strip-shaped impressions that each interconnect a respective two corner points of the blade body.

18 Claims, 4 Drawing Sheets

(56) References Cited

U.S. PATENT DOCUMENTS

| | | | | |
|---|---|---|---|---|
| 4,513,742 | A * | 4/1985 | Arnegger | A61B 17/14 30/350 |
| 5,135,533 | A * | 8/1992 | Petersen | A61B 17/15 30/345 |
| 5,306,285 | A * | 4/1994 | Miller | B23D 61/006 30/355 |
| 2002/0133186 | A1 * | 9/2002 | Kullmer | B23D 61/006 606/178 |
| 2003/0032971 | A1 * | 2/2003 | Hausmann | A61B 17/14 606/176 |
| 2004/0098000 | A1 * | 5/2004 | Kleinwaechter | A61B 17/14 D24/146 |
| 2005/0245935 | A1 * | 11/2005 | Casey | A61B 17/142 606/82 |
| 2010/0125289 | A1 * | 5/2010 | Kehr | A61B 17/3213 606/167 |

FOREIGN PATENT DOCUMENTS

| | | |
|---|---|---|
| EP | 0 695 607 A1 | 2/1996 |
| EP | 1 263 333 B1 | 12/2002 |
| WO | 01/66023 A1 | 9/2001 |

\* cited by examiner

ROTARY RECIPROCATING SAW BLADE FOR A POWER TOOL

The application is a 35 U.S.C. § 371 National Stage Application of PCT/EP2012/071980, filed on Nov. 7, 2012, which claims the benefit of priority to Ser. No. DE 10 2011 089 097.1, filed on Dec. 20, 2011 in Germany, the disclosures of which are incorporated herein by reference in their entirety.

The disclosure relates to a rotary reciprocating saw blade for a power tool.

BACKGROUND

A plunge saw blade for a power tool, which during operation performs a reciprocating rotary motion, is described in EP 1 263 333 B1. The plunge saw blade has an approximately rectangular blade body, which at one end is provided with a mounting portion for connection to the tool shaft and at the other end is provided with a cutting edge having cutting teeth. In the side face of the blade body, a multiplicity of small-area impressions are made between the receptacle for the tool shaft and the cutting edge, which are intended to help to reduce the upswing behavior of the saw blade during operation and to increase the cutting precision. The impressions have a comparatively small stamping depth and can be configured as rectangles, circles or triangles, wherein the non-round geometries have an orientation which is angled relative to the longitudinal axis of the plunge saw blade. In total, a multiplicity of impressions are made in the side face.

SUMMARY

The object of the disclosure is, with simple design measures, to configure a rotary reciprocating saw blade for a plunge saw such that, over a long period of operation, precise workpiece machining is possible.

This object is achieved according to the disclosure.

The disclosure relates to a rotary reciprocating saw blade in the form of a plunge saw blade, which can be used in power tools, in particular in hand-operated power tools, and during operation performs a rotary reciprocating motion. The plunge saw blade has a, for instance, circular-segment-shaped or rectangular, or at least approximately rectangular blade body, one side edge of which is configured as an at least approximately rectilinear, possibly slightly bent cutting edge having cutting teeth.

In at least one side face of the blade body, at least one impression, which is preferably of linear or strip-shaped configuration, is made and extends, for instance, in the direction of the cutting edge. The impression alters the tension characteristics of the blade body, whereby both the natural frequency of the plunge saw blade and the propagation of vibration waves are positively influenced. An overlap of the natural frequencies of blade body and power tool can be prevented, thereby resulting in reduced vibration of the blade body in the region of the toothed cutting edge. Overall the vibration and noise development is reduced, so that, in addition to an improvement in comfort, the machining quality, too, is raised. Due to the lower loads to which the plunge saw blade is subjected, the improved work quality can be maintained also over a longer period of operation.

In the blade body is made at least one cavity, which is delimited by at least one impression. The cavity, which can be produced, for instance, by stamping, reduces the mass moment of inertia of the blade body, which has a positive effect, in particular in view of a lesser vibration transmission, upon tool life and ease of operation. Moreover, smaller rated drive motors can be used. The impression in the blade body counteracts a reduction in stability caused by the recess. Through the combination of cavity and impression, various advantages can thus be linked, namely a reduced mass or a mass moment of inertia and improved stability with reduced vibration propagation.

Advantageously, in the blade body are made a plurality of cavities, which are respectively delimited by at least one, preferably linear or strip-shaped impression. It can be expedient to provide impressions on at least two sides of a cavity, possibly on all sides of the cavity, in order to counteract the reduction in stability as a result of the cavities.

Various cross-sectional geometries of the cavities can enter into consideration, in particular angled, for instance triangular or rectangular geometries.

Furthermore, the impression can advantageously be produced in a simple manner. The impression leads to strengthening in the blade body and, as a consequence thereof, an altered tension characteristic.

The impression can be produced by stamping; in this case an impression in the form of a depression is present on one side face of the blade body, while on the opposite side face the stamping produces a corresponding elevation. The impressions produced by stamping have a stamping depth of, preferably, at least 0.1 mm. The impressions can all be made in the same side face, so that on this side face only depressions and on the opposite side face only elevations are present. Alternatively, it is also possible to provide impressions on each side face, so that each of the two side faces has depressions and elevations.

It is also possible, however, to produce the impression by rolling, in particular by simultaneous rolling on both side faces of the blade body, by movement of the saw blade between two contrarotating rolls, so that impressions in the form of depressions are disposed on both side faces and the material in the blade body is compressed in the region of the impression. In the case of impressions created by rolling, the stamping depth is preferably one-third of the blade thickness, for instance maximally 0.2 mm or 0.1 mm, and can possibly lie within the hundredths of millimeters range, for instance 0.01 mm. Here it is also advantageous for the saw blade to be impressed from opposite sides, so that no elevations are formed on a side face of the saw blade. The rolled impressions are located on both side faces of the saw blade and are configured, in particular, in mirror symmetry to one another. The rolled impression is not in the form of a groove, but of an indentation which is barely visible or detectable from outside and which leads to a material compression in the blade body and, as a consequence thereof, to an altered tension characteristic. Accordingly, the impression does not serve to improve chip removal, heat dissipation or to reduce the frictional contact with the workpiece to be machined, but to increase the stiffness and make a desired alteration to the tension characteristic.

Variously realized impressions can enter into consideration. Linear or strip-shaped impressions, which are of either rectilinear or curved construction or can have rectilinear and curved portions, are possible. In the case of a linear impression the width is very small, while in the case of a strip-shaped impression the width is preferably maximally one-third of the blade height, for instance 3 mm, wherein larger widths, where appropriate, are also possible. In principle, planar impressions on the saw blade are also possible.

In addition, it is possible, in particular in the case of a linear impression, to produce circumferentially closed geometric patterns, for instance approximately rectangular impressions, triangular impressions or the like. The impression per se is linear or strip-shaped and forms the marginal contour of the geometric pattern.

It can be expedient, in the case of a linear or strip-shaped configuration, for the impression to extend at least in part in the longitudinal direction, i.e. parallel to the cutting edge. In principle, however, an angled orientation of the linear or strip-shaped impression in relation to the longitudinal axis, or an orthogonal course, i.e. in the transverse direction of the saw blade, is also possible. Furthermore, various patterns of impressions, which can be represented as a combination of different impressions, for instance a combination of rectilinear impressions which in part run in the longitudinal and in the transverse direction, or at an angle to the longitudinal axis, are possible.

In addition, defined patterns of impressions, which change in dependence on the axial position, are possible.

The linear or strip-shaped impressions are made in the blade body such that at least two corner points of the blade body are connected by the impressions. Preferably, all four corner points of the blade body are connected by linear or strip-shaped impressions, wherein, in principle, various construction variants can enter into consideration. It is possible, for instance, to make diagonally running impressions, which connect diagonally situated corner points of the blade body. Additionally or alternatively, a connection via longitudinally or transversely running impressions between the corner points in the blade body can enter into consideration. Both with diagonal impressions and with impressions extending in the longitudinal direction or transversely to the longitudinal direction, a framework of impressions, which significantly improves the strength of the blade body, is created. The diagonal and/or longitudinally or transversely extending impressions can run up to the respective corner parts. According to a further embodiment, it is also possible, however, for an impression of this type to be situated at a distance from one or two corner points, in which case the longitudinal axis of the impression runs through the corner points.

Where appropriate, in addition to the impressions, chemical finishing treatments can be conducted locally in the saw blade, for instance by coating, in order to influence the tension in the saw blade. Alternatively or additionally, local thermal finishing treatments, for instance induction hardening, are also possible.

BRIEF DESCRIPTION OF THE DRAWINGS

Further advantages and expedient embodiments can be derived from the description of the figures, wherein.

DETAILED DESCRIPTION

In the figures, same components are provided with same reference symbols.

Figure 1:
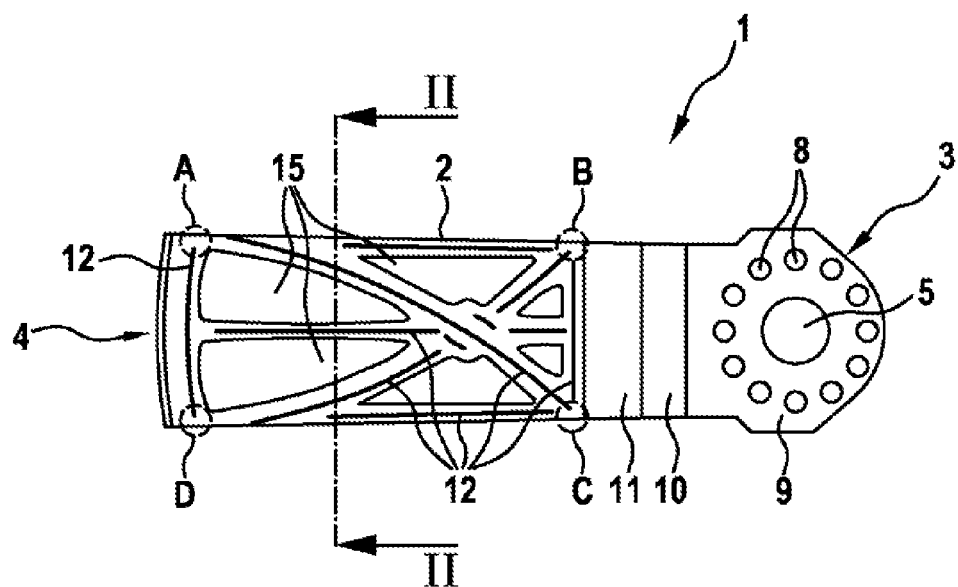
FIG. 1 shows a rotary reciprocating saw blade, realized as a plunge saw blade, comprising an approximately rectangular blade body, the front edge of which is realized as a cutting edge having cutting teeth, and comprising a mounting part for fastening to a tool shaft, and also comprising a plurality of impressions in the blade body, which delimit intervening cavities.

The plunge saw blade 1, represented in FIG. 1, for a power tool having a rotary reciprocating drive comprises an at least approximately rectangular or circular-segment-shaped blade body 2, as well as a cranked mounting part 3 connected to the blade body 2. On the free end face facing away from the mounting part 3, the blade body 2 is provided with a cutting edge 4 having cutting teeth. The mounting part 3 comprises a shaft receiving portion 9 having a fastening receptacle 5 for receiving the tool shaft 6 of the power tool, which performs a rotary reciprocating motion about the rotational axis 7. The fastening with the tool shaft 6 is effected by means of latching openings 8, which are made annularly about the central fastening recess 5 in the shaft receiving portion 9.

The mounting part 3 further comprises a transition portion 10, as well as a connecting portion 11 via which the connection to the blade body 2 is effected; blade body 2 and mounting part 3 are realized as separate components, which, however, are fixedly connected to each other. The shaft receiving portion 9 and the connecting portion 11 lie parallelly offset from each other, the height difference being bridged by the obliquely running transition portion 10. The shaft receiving portion 9, the transition portion 10 and the connecting portion 1 are configured in one piece.

As can further be seen from FIG. 1, the blade body 2 of the plunge saw blade 1 has a plurality of cavities 15, which pass fully through the blade body orthogonally to the plane of the blade body. In principle, however, cavities in the form of depressions in the blade body 2 which do not pass fully through the blade body are also possible; in this case, the depressions can be disposed either only on one side face of the blade body 2 or on both side faces, respectively in mirror symmetry or asymmetrically.

By the making of the cavities 15, the mass and the mass moment of inertia of the blade body, as well as of the plunge saw blade, are reduced. In order to at least partially compensate for the stiffness weakening associated with the cavities, in the blade body are made impressions 12, which are preferably disposed only on one side face of the blade body. The impressions 12 are applied to the side face, in particular in such a way that the cavities 15 are delimited on more than one side, preferably on all sides, by the impressions. The impressions bring about an increase in strength.

The impressions are preferably produced by stamping; in this case, impressions in the form of a depression of at least 0.1 mm are present on one side face of the blade body, while on the opposite side face the stamping produces a corresponding elevation. The impressions can also be produced, however, by rolling, so that, on both mutually opposing side faces of the blade body, impressions made in mirror-symmetrical arrangement are present, which results in compression of the blade body material. With the production of the impressions 12, no material is removed from the blade body.

In the blade body 2 of the plunge saw blade 1 are made, in total, a multiplicity of impressions 12, which extend in the longitudinal direction—orthogonally to the cutting edge 4—in the transverse direction or at an angle to the longitudinal axis, for instance diagonally. A plurality of impressions 12 run between the corner points A, B, C and D of the approximately rectangular blade body 2. The impressions 12 are of rectilinear, or—in the case of diagonally running impressions—curved construction. The virtual corner points of the blade body 2 are connected by the impressions 12, to be precise both in the diagonal direction and in the longitudinal direction or transversely to the longitudinal axis of the blade body. The connection is effected in such a way that impressions extend up to the corner points A, B, C, D or with only comparatively small distance from the corner points. In the illustrative embodiment according to FIG. 1, each corner point is intersected by a curvedly running diagonal impression, by an impression extending in the longitudinal direction and by an impression extending in the transverse direction.

The impressions 12 run along webs in the blade body 2. For the stabilization of the blade body, a middle, longitudinally extending web having an impression 12 is provided. In total, in the illustrative embodiment, six differently sized cavities 15, respectively having an at least approximately triangular geometry, are made between the impressions 12. All cavities 15 are delimited on all sides by webs or impressions 12.

Figure 2:
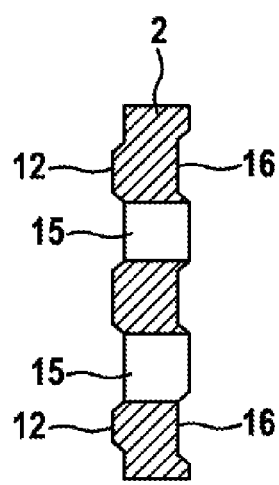
FIG. 2 shows the blade body from FIG. 1 in a section along the sectional line II-II.

As can be seen from the sectional representation according to FIG. 2, each impression 12, produced by stamping, in the form of a depression on one side face of the blade body 2 brings about a corresponding elevation 16 on the opposite side face of the blade body. The depressions or elevations delimit the intervening cavities 15.

Intersecting impressions do not lie one above the other, but rather, in this case, only one of the impressions is of continuous and the intersecting impression is of discontinuous configuration.

In total, the impressions form between the corner points A, B, C, D a frame-like design, which significantly improves the strength of the blade body 2. It can in principle be sufficient to connect the corner points, for instance, only by diagonals, or, alternatively hereto, only by longitudinally or transversely extending impressions. In addition, it is possible, as represented in the illustrative embodiments according to FIGS. 1, 3 and 4, to connect the corner points both by diagonally running impressions and by longitudinally and transversely running impressions.

According to FIG. 1, the diagonally running impressions extend respectively between diagonally opposing corner points A, C and B, D, whereas longitudinally extending impressions are configured such that they are abbreviated, at least at the corner points A, D adjacent to the front cutting edge 4, and have a greater distance from these corner points. Nevertheless, the longitudinal axes of the impressions 12, which extend in the longitudinal direction, intersect the corner points in spite of a distance which may be present.

In the illustrative embodiment according to FIG. 2, the blade body 2 of the plunge saw blade 1 has a fundamentally similar form as in the illustrative embodiment according to FIG. 1. However, in the illustrative embodiment according to FIG. 3, the diagonally running impressions 12 do not extend up to the front corner points, but have a distance from these. In contrast, the marginal, longitudinally running impressions extend up to the front and also the rear corner points.

The marginal impressions which run in the longitudinal direction also have an at least slight distance from the respective side edge of the blade body 2.

The transversely running impressions on the side adjacent to the cutting edge 4 or the side adjacent to the mounting part 3 extend over the entire width of the blade body 2. In FIG. 1, by contrast, the transversely running impressions have a distance from each side edge.

Figure 3:
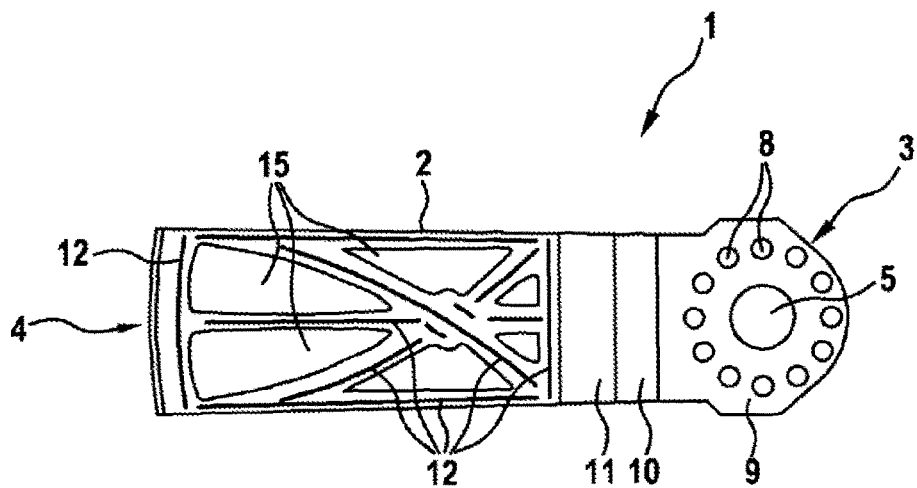
FIG. 3 shows a plunge saw blade in a further embodiment.
Figure 4:
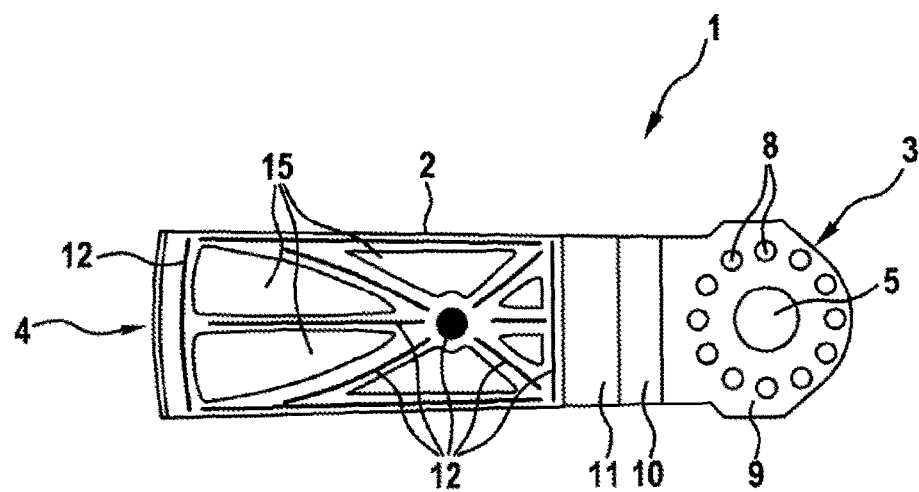
FIG. 4 shows the plunge saw blade in a further embodiment.

In FIG. 4, the blade body 2 is configured substantially the same as in FIG. 3, yet with the difference that the intersecting, diagonally running impressions are both interrupted at the point of intersection, wherein, in the region of the point of intersection, a small circular, planar impression is made.

Figure 5:
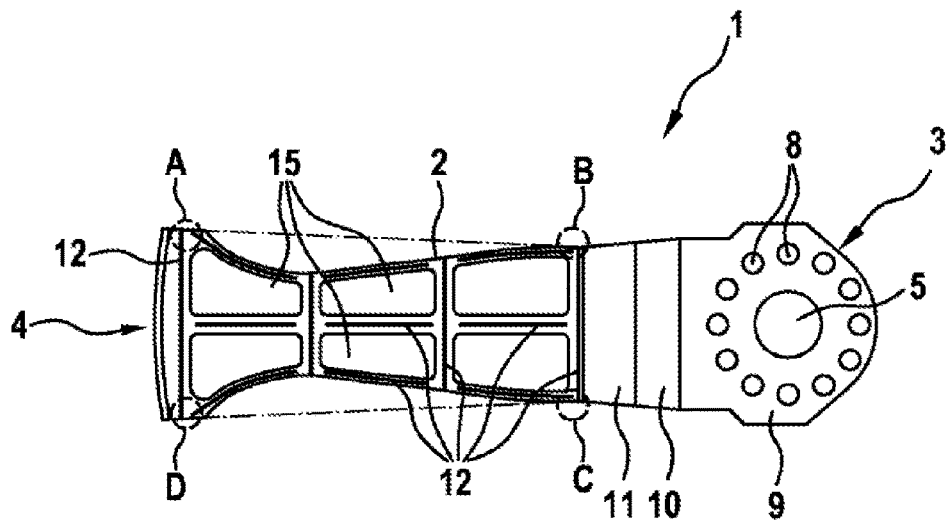
FIG. 5 shows a plunge saw blade, the blade body of which has lateral indentations and is provided with impressions and cavities.
Figure 6:
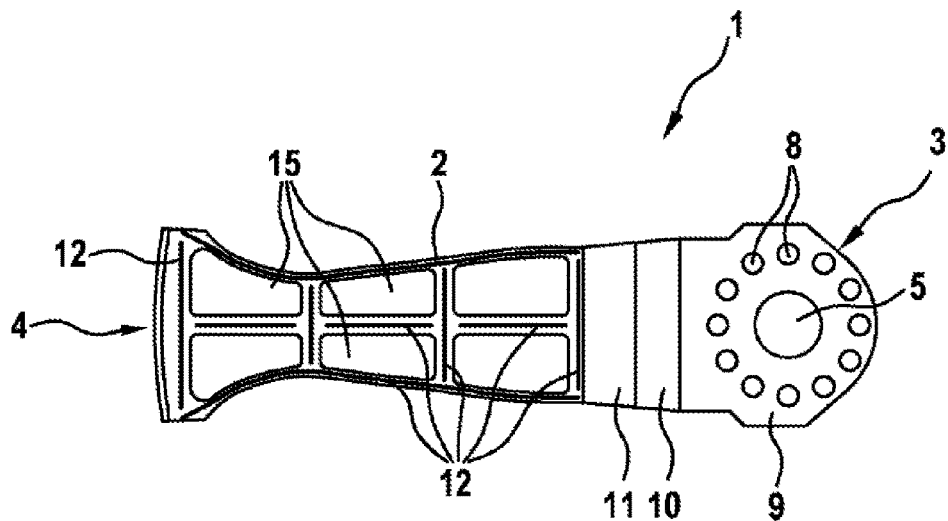
FIG. 6 shows a similar plunge saw blade to FIG. 5, yet with differently realized impressions.
Figure 7:
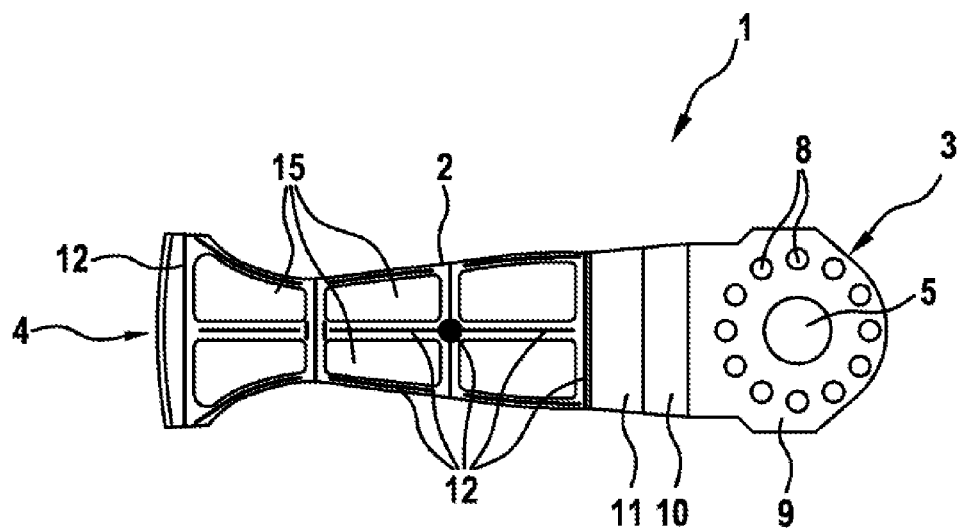
FIG. 7 shows yet a further plunge saw blade according to FIG. 5 or 6 with impressions, in yet a further construction variant.

In FIGS. 5 to 7, further illustrative embodiments of plunge saw blades 1 are represented. The blade bodies 2 of the plunge saw blades have in relation to the connecting line between the front and rear corner point A, B or C, D a lateral indentation, whereby the weight and the moment of inertia of the plunge saw blade 1 is further reduced. As in the first illustrative embodiments, according to FIGS. 5 to 7, also, the impressions 12 extend between the corner points A, B, C, D of the blade body 2. Due to the non-rectilinear side edge of the blade body 2, also the impressions running directly adjacent and parallel to the side edge are, at least in part, of curved construction. In addition there are, in a middle, longitudinally extending web, a plurality of impression portions, as well as, in transversely extending webs, impressions between the two side edges. The front situated side edges A, D, as well as the rear situated corner points B, C, are respectively intersected by transversely extending impressions.

In the blade body 2 are made, in total, six cavities 15, which are respectively delimited on each side by impressions 12. The cavities 15 have an approximately square shape, wherein, in the region of the strongest curvature of the side edge of the blade body 2, the cavities too possess a correspondingly curved side line.

In the illustrative embodiment according to FIG. 5, the transversely running impressions 12 extend between the front corner points A, D or the rear corner points B, C over the entire width of the blade body; the same applies to the illustrative embodiment according to FIG. 7, whereas, according to FIG. 6, the impressions 12 lie between the front or rear corner points at a distance from the corner points and the impressions extending along the side edges run up to the corner points.

From FIG. 7 can additionally be seen that, in the region of intersection of longitudinally and transversely running impressions, diverse interruptions can be present. For example, a planar, oval or circular impression, which lies on the middle, longitudinally extending web, or an offsetting of the longitudinally extending impression by means of two short, smaller impression portions present on both sides of the transversely extending impression, is possible.

The invention claimed is:

1. A rotary reciprocating saw blade for a power tool, comprising:
 a blade body having an at least four-cornered shape defining:
  an at least approximately rectilinear cutting edge;
  at least one cavity that extends through the blade body; and
  a plurality of linear or strip-shaped impressions in the blade body, the impressions located such that each side of the at least one cavity is delimited by a respective impression, and such that each corner of the blade body is connected to at least one other corner of the blade body by a further respective impression.

2. The rotary reciprocating saw blade as claimed in claim 1, wherein at least two of the impressions run in respective diagonal directions, such that diagonally situated corners of the blade body are connected by a respective diagonally running impression.

3. The rotary reciprocating saw blade as claimed in claim 1, wherein:
the blade body further has a first side face and a second side face opposite the first side face; and
each impression includes a depression in the first side face and a corresponding elevation in the second side face.

4. The rotary reciprocating saw blade as claimed in claim 3, wherein:
the impressions are at least one of:
longitudinally running impressions; and
transversely running impressions.

5. The rotary reciprocating saw blade as claimed in claim 3, wherein at least one of the impressions is formed by stamping in the first side face of the blade body.

6. The rotary reciprocating saw blade as claimed in claim 3, wherein a depth of the depression in each of the impressions is at least 0.1 mm.

7. The rotary reciprocating saw blade as claimed in claim 3, wherein a width of each of the impressions is maximally one-third of a blade height.

8. The rotary reciprocating saw blade as claimed in claim 3, wherein the rotary reciprocating saw blade has local chemical finishing treatments.

9. The rotary reciprocating saw blade as claimed in claim 3, wherein the rotary reciprocating saw blade has local thermal finishing treatments.

10. The rotary reciprocating saw blade as claimed in claim 1, wherein:
the at least one cavity includes a plurality of cavities; and
at least two of the plurality of cavities are separated by one or more of the impressions.

11. A rotary reciprocating saw blade for a power tool, comprising:
a blade body having:
a cutting edge;
a plurality of linear or strip-shaped impressions that includes:
a first impression that is adjacent to and substantially parallel with the cutting edge;
a second impression that is distal to and substantially parallel with the cutting edge;
a pair of third and fourth impressions that each extend from a respective end of the first impression to a corresponding end of the second impression and define a respective lateral side of the blade body;
a fifth impression that extends from a midpoint of the first impression to a midpoint of the second impression along a midline of the blade body; and
at least one sixth impression that extends from the third impression to the fourth impression; and
a plurality of cavities that extend through the blade body, each cavity positioned so that each side of the cavity is delimited by a respective one of the plurality of impressions.

12. The rotary reciprocating saw blade of claim 11, wherein the third and fourth impressions are substantially rectilinear.

13. The rotary reciprocating saw blade of claim 12, wherein the at least one sixth impression includes a pair of diagonal impressions that extend from a respective end of the third impression to a corresponding diagonally opposite end of the fourth impression.

14. The rotary reciprocating saw blade of claim 11, wherein the blade body further has a circular impression located at an intersection of the fifth impression and the at least one sixth impression.

15. The rotary reciprocating saw blade of claim 11, wherein the third and fourth impressions curve toward each other in a middle portion of the blade body.

16. The rotary reciprocating saw blade of claim 15, wherein the at least one sixth impression is substantially parallel to the cutting edge.

17. The rotary reciprocating saw blade of claim 11, wherein the plurality of cavities includes six cavities that are symmetrically disposed along the midline of the blade body.

18. A power tool, comprising:
a rotary reciprocating saw blade including:
a blade body having an at least four-cornered shape defining:
an at least approximately rectilinear cutting edge;
a first side face;
a second side face opposite the first side face;
at least one cavity that extends through the blade body from the first side face to the second side face; and
a plurality of linear or strip-shaped impressions, the impressions located such that each side of the at least one cavity is delimited by a respective impression, and such that each corner of the blade body is connected to at least one other corner of the blade body by a further respective impression, each impression including a depression in the first side face and a corresponding elevation in the second side face.

* * * * *